US008722783B2

(12) United States Patent
Rose et al.

(10) Patent No.: US 8,722,783 B2
(45) Date of Patent: May 13, 2014

(54) FIBER REINFORCED COMPOSITE MATERIAL

(75) Inventors: John Rose, Collierville, TN (US); Malcolm Brown, Otley (GB); Nicola Macauley, Haxby (GB); Michael Hall, Linthorpe (GB)

(73) Assignee: Smith & Nephew, Inc., Memphis, TN (US)

( * ) Notice: Subject to any disclaimer, the term of this patent is extended or adjusted under 35 U.S.C. 154(b) by 517 days.

(21) Appl. No.: 12/516,573

(22) PCT Filed: Nov. 30, 2007

(86) PCT No.: PCT/US2007/086067
§ 371 (c)(1),
(2), (4) Date: Feb. 8, 2010

(87) PCT Pub. No.: WO2008/067531
PCT Pub. Date: Jun. 5, 2008

(65) Prior Publication Data
US 2010/0137491 A1   Jun. 3, 2010

Related U.S. Application Data

(60) Provisional application No. 60/867,978, filed on Nov. 30, 2006.

(51) Int. Cl.
*C08K 3/26* (2006.01)

(52) U.S. Cl.
USPC ............ 524/417; 524/599; 524/425; 524/424

(58) Field of Classification Search
USPC ........................................................ 524/417
See application file for complete search history.

(56) References Cited

U.S. PATENT DOCUMENTS

| | | | |
|---|---|---|---|
| 3,531,561 A | 9/1970 | Trehu | |
| 3,636,956 A | 1/1972 | Schneider | |
| 3,736,646 A | 6/1973 | Schmitt et al. | |
| 3,797,499 A | 3/1974 | Schneider | |
| 4,137,921 A | 2/1979 | Okuzumi et al. | |
| 4,181,983 A | 1/1980 | Kulkarni | |
| 4,356,228 A * | 10/1982 | Kobayashi et al. | ............ 428/327 |
| 4,438,253 A | 3/1984 | Casey et al. | |
| 4,523,591 A | 6/1985 | Kaplan et al. | |
| 4,539,981 A | 9/1985 | Tung | |
| 4,559,945 A | 12/1985 | Koelmel et al. | |
| 4,636,215 A | 1/1987 | Schwartz | |
| 4,700,704 A | 10/1987 | Jamiolkowski et al. | |
| 4,756,307 A | 7/1988 | Crowninshield | |
| 4,916,207 A | 4/1990 | Boyle, Jr. et al. | |
| 4,938,763 A | 7/1990 | Dunn et al. | |
| 4,950,258 A | 8/1990 | Kawai et al. | |
| 4,968,317 A | 11/1990 | Tormala et al. | |
| 4,990,161 A | 2/1991 | Kampner | |
| 5,010,145 A * | 4/1991 | Ikada et al. | .................... 525/415 |
| 5,049,591 A | 9/1991 | Hayashi et al. | |
| 5,053,035 A | 10/1991 | McLaren | |
| 5,108,755 A | 4/1992 | Daniels et al. | |
| 5,110,852 A | 5/1992 | Gogolewski et al. | |
| 5,192,301 A | 3/1993 | Kamiya et al. | |
| 5,201,771 A | 4/1993 | Belykh et al. | |
| 5,250,584 A | 10/1993 | Ikada et al. | |
| 5,266,608 A | 11/1993 | Katz et al. | |
| 5,275,601 A | 1/1994 | Gogolewski et al. | |
| 5,294,395 A | 3/1994 | Broyer | |
| 5,333,624 A | 8/1994 | Tovey | |
| 5,360,448 A | 11/1994 | Thramann | |
| 5,364,400 A | 11/1994 | Rego, Jr. et al. | |
| 5,376,120 A | 12/1994 | Sarver et al. | |
| 5,383,931 A | 1/1995 | Hehli et al. | |
| 5,407,445 A | 4/1995 | Tautvydas et al. | |
| 5,417,712 A | 5/1995 | Whittaker et al. | |
| 5,437,918 A | 8/1995 | Taniguchi et al. | |
| 5,441,515 A | 8/1995 | Khosravi et al. | |
| 5,458,653 A | 10/1995 | Davidson | |
| 5,470,334 A | 11/1995 | Ross et al. | |
| 5,525,706 A | 6/1996 | Gruber et al. | |
| 5,527,337 A | 6/1996 | Stack et al. | |
| 5,527,341 A | 6/1996 | Gogolewski et al. | |
| 5,562,704 A | 10/1996 | Tamminmaki et al. | |
| 5,569,250 A | 10/1996 | Sarver et al. | |
| 5,571,193 A | 11/1996 | Kampner | |
| 5,571,204 A | 11/1996 | Nies | |
| 5,633,002 A | 5/1997 | Stricker et al. | |
| 5,634,936 A | 6/1997 | Linden et al. | |

(Continued)

FOREIGN PATENT DOCUMENTS

| | | |
|---|---|---|
| CA | 2254002 | 5/2000 |
| CN | 1857742 | 11/2006 |

(Continued)

OTHER PUBLICATIONS

First Office Action issued by the State Intellectual Property Office in related Chinese Patent Application No. 200780043841.9.

(Continued)

*Primary Examiner* — Doris Lee
(74) *Attorney, Agent, or Firm* — Krieg DeVault LLP

(57) ABSTRACT

The present disclosure relates to a fiber reinforced composite material. In an embodiment, the composite material includes a PLLA fiber material and a matrix material that does not have the same chemical element composition as the fiber material. Other fiber reinforced composite materials are also disclosed.

38 Claims, No Drawings

(56) References Cited

U.S. PATENT DOCUMENTS

| | | |
|---|---|---|
| 5,641,502 A | 6/1997 | Skalla et al. |
| 5,660,846 A | 8/1997 | Cheikh |
| 5,665,831 A | 9/1997 | Neuenschwander et al. |
| 5,670,161 A | 9/1997 | Healy et al. |
| 5,676,699 A | 10/1997 | Gogolewski et al. |
| 5,690,671 A | 11/1997 | McGurk et al. |
| 5,695,497 A | 12/1997 | Stahelin |
| 5,700,901 A | 12/1997 | Hurst et al. |
| 5,716,410 A | 2/1998 | Wang et al. |
| 5,716,413 A | 2/1998 | Walter et al. |
| 5,733,330 A | 3/1998 | Cox |
| 5,741,329 A | 4/1998 | Agrawal et al. |
| 5,760,118 A | 6/1998 | Sinclair et al. |
| 5,766,239 A | 6/1998 | Cox |
| 5,766,618 A | 6/1998 | Laurencin et al. |
| 5,792,400 A | 8/1998 | Talja et al. |
| 5,817,328 A | 10/1998 | Gresser et al. |
| 5,834,582 A | 11/1998 | Sinclair et al. |
| 5,837,276 A | 11/1998 | Cheikh |
| 5,853,639 A | 12/1998 | Kawakami et al. |
| 5,863,297 A | 1/1999 | Walter et al. |
| 5,868,746 A | 2/1999 | Sarver et al. |
| 5,893,850 A | 4/1999 | Cachia |
| 5,902,599 A | 5/1999 | Anseth et al. |
| 5,904,658 A | 5/1999 | Niederauer et al. |
| 5,908,918 A | 6/1999 | Chen et al. |
| 5,935,172 A | 8/1999 | Ochoa et al. |
| 5,939,453 A | 8/1999 | Heller et al. |
| 5,947,893 A | 9/1999 | Agrawal et al. |
| 5,968,092 A | 10/1999 | Buscemi et al. |
| 5,977,204 A | 11/1999 | Boyan et al. |
| 5,980,564 A | 11/1999 | Stinson |
| 5,997,580 A | 12/1999 | Mastrorio et al. |
| 5,997,582 A | 12/1999 | Weiss |
| 6,001,100 A | 12/1999 | Sherman et al. |
| 6,001,101 A | 12/1999 | Augagneur et al. |
| 6,005,161 A | 12/1999 | Brekke et al. |
| 6,027,742 A * | 2/2000 | Lee et al. .............. 424/422 |
| 6,071,982 A | 6/2000 | Wise et al. |
| 6,077,989 A | 6/2000 | Kandel et al. |
| 6,113,624 A | 9/2000 | Bezwada et al. |
| 6,136,369 A | 10/2000 | Leitao et al. |
| 6,139,963 A * | 10/2000 | Fujii et al. .............. 428/407 |
| 6,150,497 A | 11/2000 | Sastry et al. |
| 6,156,842 A | 12/2000 | Hoenig et al. |
| 6,160,084 A | 12/2000 | Langer et al. |
| 6,162,225 A | 12/2000 | Gertzman et al. |
| 6,168,570 B1 | 1/2001 | Ferrera |
| 6,179,842 B1 | 1/2001 | Spotorno et al. |
| 6,203,573 B1 | 3/2001 | Walter et al. |
| 6,206,883 B1 | 3/2001 | Tunc |
| 6,248,108 B1 | 6/2001 | Tormala et al. |
| 6,248,430 B1 | 6/2001 | Toyoda et al. |
| 6,281,262 B1 | 8/2001 | Shikinami |
| 6,283,973 B1 | 9/2001 | Hubbard et al. |
| 6,293,950 B1 | 9/2001 | Lynch et al. |
| 6,299,448 B1 | 10/2001 | Zdrahala et al. |
| 6,303,697 B1 | 10/2001 | Yuan et al. |
| 6,315,788 B1 | 11/2001 | Roby |
| 6,344,496 B1 | 2/2002 | Niederauer et al. |
| 6,375,465 B1 | 4/2002 | Engman et al. |
| 6,388,043 B1 | 5/2002 | Langer et al. |
| 6,425,923 B1 | 7/2002 | Stalcup et al. |
| 6,436,136 B1 | 8/2002 | Flodin et al. |
| 6,447,515 B1 | 9/2002 | Meldrum |
| 6,468,277 B1 | 10/2002 | Justin et al. |
| 6,486,296 B1 | 11/2002 | Shimamoto et al. |
| 6,503,278 B1 | 1/2003 | Pohjonen et al. |
| 6,503,991 B2 | 1/2003 | Shalaby |
| 6,511,511 B1 | 1/2003 | Slivka et al. |
| 6,511,748 B1 * | 1/2003 | Barrows .............. 428/373 |
| 6,514,286 B1 | 2/2003 | Leatherbury et al. |
| 6,547,792 B1 | 4/2003 | Tsuji et al. |
| 6,565,606 B1 | 5/2003 | Bruce et al. |
| 6,579,533 B1 | 6/2003 | Tormala et al. |
| 6,599,323 B2 | 7/2003 | Melican et al. |
| 6,605,090 B1 | 8/2003 | Trieu et al. |
| 6,613,089 B1 | 9/2003 | Estes et al. |
| 6,623,487 B1 | 9/2003 | Goshert |
| 6,652,582 B1 | 11/2003 | Stinson |
| 6,716,957 B2 | 4/2004 | Tunc |
| 6,719,935 B2 | 4/2004 | Tunc |
| 6,720,402 B2 | 4/2004 | Langer et al. |
| 6,726,696 B1 | 4/2004 | Houser et al. |
| 6,758,862 B2 | 7/2004 | Berry et al. |
| 6,758,863 B2 | 7/2004 | Estes et al. |
| 6,783,712 B2 | 8/2004 | Slivka et al. |
| 6,827,743 B2 | 12/2004 | Eisermann et al. |
| 6,830,575 B2 | 12/2004 | Stenzel et al. |
| 6,841,111 B2 | 1/2005 | Rickner et al. |
| 6,843,799 B2 | 1/2005 | Bartlett |
| 6,852,825 B2 | 2/2005 | Lendlein et al. |
| 6,869,445 B1 | 3/2005 | Johnson |
| 6,881,766 B2 | 4/2005 | Hain |
| 6,902,584 B2 | 6/2005 | Kwan et al. |
| 6,908,466 B1 | 6/2005 | Bonutti et al. |
| 6,916,321 B2 | 7/2005 | TenHuisen et al. |
| 6,974,862 B2 | 12/2005 | Ringeisen et al. |
| 7,012,106 B2 | 3/2006 | Yuan et al. |
| 7,033,603 B2 | 4/2006 | Nelson et al. |
| 7,192,443 B2 | 3/2007 | Solem et al. |
| 7,208,550 B2 | 4/2007 | Mather et al. |
| 7,214,765 B2 | 5/2007 | Ringeisen et al. |
| 7,261,716 B2 | 8/2007 | Strobel et al. |
| 7,261,734 B2 | 8/2007 | Gellman et al. |
| 7,268,205 B2 | 9/2007 | Williams et al. |
| 7,270,813 B2 | 9/2007 | Shimp et al. |
| 7,285,087 B2 | 10/2007 | Moaddeb et al. |
| 7,285,130 B2 | 10/2007 | Austin |
| 7,314,480 B2 | 1/2008 | Eidenschink et al. |
| 7,335,375 B2 | 2/2008 | Li et al. |
| 7,378,144 B2 | 5/2008 | DeMeo et al. |
| 7,455,674 B2 | 11/2008 | Rose |
| 7,524,891 B2 | 4/2009 | Rose |
| 2001/0012940 A1 | 8/2001 | Tunc |
| 2001/0018614 A1 | 8/2001 | Bianchi |
| 2002/0022588 A1 | 2/2002 | Wilkie et al. |
| 2002/0029041 A1 | 3/2002 | Hover et al. |
| 2002/0029043 A1 | 3/2002 | Ahrens et al. |
| 2002/0071822 A1 | 6/2002 | Uhrich |
| 2002/0082362 A1 | 6/2002 | Broccini et al. |
| 2002/0120348 A1 | 8/2002 | Melican et al. |
| 2002/0138154 A1 | 9/2002 | Li et al. |
| 2002/0150775 A1 | 10/2002 | Ishikawa et al. |
| 2002/0160032 A1 | 10/2002 | Long et al. |
| 2003/0045941 A1 | 3/2003 | Lewallen |
| 2003/0055198 A1 | 3/2003 | Langer et al. |
| 2003/0104031 A1 | 6/2003 | Dumont et al. |
| 2003/0114937 A1 | 6/2003 | Leatherbury et al. |
| 2003/0120280 A1 | 6/2003 | Roller et al. |
| 2003/0125745 A1 | 7/2003 | Tseng et al. |
| 2003/0130742 A1 | 7/2003 | Connelly et al. |
| 2003/0153971 A1 | 8/2003 | Chandrasekaran |
| 2003/0153972 A1 | 8/2003 | Helmus |
| 2003/0180344 A1 | 9/2003 | Wise et al. |
| 2003/0236573 A1 | 12/2003 | Evans et al. |
| 2004/0002770 A1 | 1/2004 | King et al. |
| 2004/0015187 A1 | 1/2004 | Lendlein et al. |
| 2004/0019386 A1 | 1/2004 | Ferree |
| 2004/0028655 A1 * | 2/2004 | Nelson et al. .............. 424/93.2 |
| 2004/0030342 A1 | 2/2004 | Trieu et al. |
| 2004/0052992 A1 | 3/2004 | Boone et al. |
| 2004/0054372 A1 | 3/2004 | Corden et al. |
| 2004/0078090 A1 * | 4/2004 | Binette et al. .............. 623/23.76 |
| 2004/0106734 A1 | 6/2004 | Rose |
| 2004/0109823 A1 | 6/2004 | Kaplan |
| 2004/0110285 A1 | 6/2004 | Lendlein et al. |
| 2004/0115239 A1 | 6/2004 | Shastri et al. |
| 2004/0131681 A1 | 7/2004 | Ambrose et al. |
| 2004/0143221 A1 | 7/2004 | Shadduck |
| 2004/0153075 A1 | 8/2004 | Roger |
| 2004/0156878 A1 | 8/2004 | Rezania et al. |
| 2004/0172118 A1 | 9/2004 | Gibson |
| 2004/0193154 A1 | 9/2004 | Leatherbury et al. |

(56) References Cited

U.S. PATENT DOCUMENTS

| | | |
|---|---|---|
| 2004/0241203 A1 | 12/2004 | Shakesheff et al. |
| 2004/0242722 A1* | 12/2004 | Rose et al. ............ 523/113 |
| 2004/0254639 A1 | 12/2004 | Li et al. |
| 2004/0258732 A1 | 12/2004 | Shikinami |
| 2004/0259972 A1 | 12/2004 | Ringeisen et al. |
| 2004/0260398 A1 | 12/2004 | Kelman |
| 2004/0265385 A1 | 12/2004 | West |
| 2004/0267263 A1 | 12/2004 | May |
| 2005/0008672 A1 | 1/2005 | Winterbottom et al. |
| 2005/0013793 A1 | 1/2005 | Beckman et al. |
| 2005/0019404 A1 | 1/2005 | Sung et al. |
| 2005/0033295 A1 | 2/2005 | Wisnewski |
| 2005/0043751 A1 | 2/2005 | Phan et al. |
| 2005/0043752 A1 | 2/2005 | Phan et al. |
| 2005/0070928 A1 | 3/2005 | Heino et al. |
| 2005/0080483 A1 | 4/2005 | Solem et al. |
| 2005/0080489 A1 | 4/2005 | Estes et al. |
| 2005/0085313 A1 | 4/2005 | Nishitani |
| 2005/0085812 A1 | 4/2005 | Sherman et al. |
| 2005/0090861 A1 | 4/2005 | Porter |
| 2005/0107886 A1 | 5/2005 | Crabtree et al. |
| 2005/0123582 A1 | 6/2005 | Sung et al. |
| 2005/0125051 A1 | 6/2005 | Eidenschink et al. |
| 2005/0136764 A1 | 6/2005 | Sherman et al. |
| 2005/0137611 A1 | 6/2005 | Escudero et al. |
| 2005/0137715 A1 | 6/2005 | Phan et al. |
| 2005/0159812 A1 | 7/2005 | Dinger, III et al. |
| 2005/0165128 A1 | 7/2005 | Cohn et al. |
| 2005/0177144 A1 | 8/2005 | Phan et al. |
| 2005/0177245 A1 | 8/2005 | Leatherbury et al. |
| 2005/0182411 A1 | 8/2005 | DeMeo et al. |
| 2005/0182428 A1 | 8/2005 | Bearinger et al. |
| 2005/0187602 A1 | 8/2005 | Eidenschink |
| 2005/0197422 A1 | 9/2005 | Mayadunne et al. |
| 2005/0208094 A1* | 9/2005 | Armitage et al. ............ 424/423 |
| 2005/0209705 A1 | 9/2005 | Niederauer et al. |
| 2005/0240281 A1 | 10/2005 | Slivka et al. |
| 2005/0273106 A1 | 12/2005 | Oepen |
| 2006/0051394 A1 | 3/2006 | Moore et al. |
| 2006/0067973 A1 | 3/2006 | Schachter |
| 2006/0121084 A1 | 6/2006 | Borden et al. |
| 2006/0121087 A1 | 6/2006 | Williams et al. |
| 2006/0136071 A1 | 6/2006 | Maspero et al. |
| 2006/0149248 A1 | 7/2006 | Schlienger et al. |
| 2006/0177480 A1 | 8/2006 | Sung et al. |
| 2006/0178748 A1 | 8/2006 | Dinger, III et al. |
| 2006/0188546 A1 | 8/2006 | Giroux |
| 2006/0188547 A1 | 8/2006 | Bezwada |
| 2006/0200150 A1* | 9/2006 | Ilomaki et al. ............ 606/73 |
| 2006/0247610 A1 | 11/2006 | Lanphere et al. |
| 2006/0263335 A1 | 11/2006 | France et al. |
| 2006/0264948 A1 | 11/2006 | Williams |
| 2006/0293749 A1 | 12/2006 | Hudgins et al. |
| 2007/0005094 A1 | 1/2007 | Eaton et al. |
| 2007/0014831 A1 | 1/2007 | Sung et al. |
| 2007/0041950 A1 | 2/2007 | Leatherbury et al. |
| 2007/0043376 A1 | 2/2007 | Leatherbury et al. |
| 2007/0043433 A1 | 2/2007 | Chandrasekaran |
| 2007/0048383 A1 | 3/2007 | Helmus |
| 2007/0050018 A1 | 3/2007 | Wainwright |
| 2007/0065652 A1 | 3/2007 | Liebschner |
| 2007/0067043 A1 | 3/2007 | Dericks |
| 2007/0100449 A1 | 5/2007 | O'Neil et al. |
| 2007/0128154 A1 | 6/2007 | Hadba et al. |
| 2007/0134305 A1 | 6/2007 | Zilberman |
| 2007/0141111 A1 | 6/2007 | Suokas et al. |
| 2007/0156251 A1 | 7/2007 | Karmon |
| 2007/0162019 A1 | 7/2007 | Burns et al. |
| 2007/0182041 A1 | 8/2007 | Rizk et al. |
| 2007/0191963 A1 | 8/2007 | Winterbottom et al. |
| 2007/0255422 A1* | 11/2007 | Wei et al. ............ 623/23.51 |
| 2007/0260324 A1 | 11/2007 | Joshi et al. |
| 2007/0265622 A1 | 11/2007 | Aeschlimann et al. |
| 2007/0270852 A1 | 11/2007 | Tormala et al. |
| 2007/0276366 A1 | 11/2007 | Gaines, Jr. |
| 2007/0280983 A1 | 12/2007 | Strickler et al. |
| 2007/0299151 A1 | 12/2007 | Guelcher et al. |
| 2007/0299156 A1 | 12/2007 | Brown |
| 2007/0299449 A1 | 12/2007 | Allinniemi et al. |
| 2008/0015578 A1 | 1/2008 | Erickson et al. |
| 2008/0077140 A1 | 3/2008 | Osman |
| 2008/0085297 A1 | 4/2008 | Dave et al. |
| 2008/0086199 A1 | 4/2008 | Dave et al. |
| 2008/0154368 A1 | 6/2008 | Justis et al. |
| 2008/0154373 A1 | 6/2008 | Protopsaltis et al. |
| 2008/0200638 A1 | 8/2008 | Redepenning |
| 2008/0206297 A1 | 8/2008 | Roeder et al. |
| 2008/0234754 A1 | 9/2008 | McCarthy et al. |
| 2008/0234762 A1 | 9/2008 | Forstein et al. |
| 2008/0241211 A1 | 10/2008 | Han et al. |
| 2008/0249633 A1 | 10/2008 | Wu |
| 2008/0262613 A1 | 10/2008 | Gogolewski |
| 2008/0305144 A1 | 12/2008 | Brown et al. |
| 2009/0048145 A1 | 2/2009 | Hellerbrand et al. |
| 2009/0093888 A1 | 4/2009 | Dawson et al. |
| 2009/0099600 A1 | 4/2009 | Moore et al. |
| 2009/0149856 A1 | 6/2009 | Paakinaho et al. |
| 2009/0171064 A1 | 7/2009 | Arimura et al. |
| 2009/0204116 A1 | 8/2009 | Shalaby et al. |
| 2009/0258965 A1 | 10/2009 | Lassila et al. |
| 2009/0270923 A1 | 10/2009 | Tormala et al. |
| 2009/0274742 A1 | 11/2009 | Brown |

FOREIGN PATENT DOCUMENTS

| | | |
|---|---|---|
| DE | 2817778 | 11/1978 |
| DE | 2947985 | 9/1981 |
| DE | 3936188 | 5/1990 |
| DE | 4226465 | 2/1993 |
| DE | 4220216 | 1/1994 |
| EP | 0204931 | 12/1986 |
| EP | 0299004 | 1/1989 |
| EP | 0321389 | 6/1989 |
| EP | 326426 | 8/1989 |
| EP | 0401844 | 12/1990 |
| EP | 0439892 | 8/1991 |
| EP | 475077 | 3/1992 |
| EP | 0590656 | 4/1994 |
| EP | 0595956 | 5/1994 |
| EP | 326426 | 12/1994 |
| EP | 0635274 | 1/1995 |
| EP | 0531487 | 1/1996 |
| EP | 0711534 | 5/1996 |
| EP | 747072 | 12/1996 |
| EP | 0751165 | 1/1997 |
| EP | 0803521 | 10/1997 |
| EP | 0805175 | 11/1997 |
| EP | 0806283 | 11/1997 |
| EP | 1009448 | 6/2000 |
| EP | 1056487 | 12/2000 |
| EP | 1086711 | 3/2001 |
| EP | 1136510 | 9/2001 |
| EP | 1142597 | 10/2001 |
| EP | 1093774 | 6/2002 |
| EP | 1216717 | 6/2002 |
| EP | 1277482 | 1/2003 |
| EP | 0815809 | 3/2004 |
| EP | 1284756 | 9/2004 |
| FR | 2707477 | 1/1995 |
| GB | 807589 | 1/1959 |
| GB | 2215209 | 9/1989 |
| JP | 2169612 | 6/1990 |
| JP | 8196617 | 8/1996 |
| JP | 9040761 | 2/1997 |
| JP | 9095606 | 4/1997 |
| JP | 9221539 | 8/1997 |
| JP | 9234241 | 9/1997 |
| JP | 9272790 | 10/1997 |
| JP | 10176039 | 6/1998 |
| JP | 10309313 | 11/1998 |
| JP | 11209595 | 8/1999 |
| JP | 3503045 | 3/2004 |
| KR | 141988 | 3/1998 |
| WO | WO8404311 | 11/1984 |

(56) References Cited

FOREIGN PATENT DOCUMENTS

| | | |
|---|---|---|
| WO | WO9003768 | 4/1990 |
| WO | WO9301773 | 2/1993 |
| WO | WO9534331 | 12/1995 |
| WO | WO9705193 | 2/1997 |
| WO | WO9725936 | 7/1997 |
| WO | WO9736555 | 10/1997 |
| WO | WO9826814 | 6/1998 |
| WO | WO9830141 | 7/1998 |
| WO | WO9847445 | 10/1998 |
| WO | WO9911296 | 3/1999 |
| WO | WO9911297 | 3/1999 |
| WO | WO9922770 | 5/1999 |
| WO | WO0001426 | 1/2000 |
| WO | WO01046501 | 6/2001 |
| WO | WO0196105 | 12/2001 |
| WO | WO0200137 | 1/2002 |
| WO | WO0234159 | 5/2002 |
| WO | WO0234310 | 5/2002 |
| WO | WO02076725 | 10/2002 |
| WO | WO03004071 | 1/2003 |
| WO | WO03064531 | 8/2003 |
| WO | WO2004011054 | 2/2004 |
| WO | WO2004071356 | 8/2004 |
| WO | WO2004110313 | 12/2004 |
| WO | WO2005014718 | 2/2005 |
| WO | WO2005028534 | 3/2005 |
| WO | WO2005046470 | 5/2005 |
| WO | WO2005085313 | 9/2005 |
| WO | WO2005112804 | 12/2005 |
| WO | WO2006053936 | 5/2006 |
| WO | WO2006064025 | 6/2006 |
| WO | WO2006108114 | 10/2006 |
| WO | WO2006114483 | 11/2006 |
| WO | WO2006116129 | 11/2006 |
| WO | WO2007010092 | 1/2007 |
| WO | WO2007020430 | 2/2007 |
| WO | WO2007021593 | 2/2007 |
| WO | WO2007023296 | 3/2007 |
| WO | WO2007024492 | 3/2007 |
| WO | WO2007065074 | 6/2007 |
| WO | WO2007084609 | 7/2007 |
| WO | WO2007086832 | 8/2007 |
| WO | WO2007111808 | 10/2007 |
| WO | WO2007117499 | 10/2007 |
| WO | WO2008001633 | 1/2008 |
| WO | WO2008116591 | 3/2008 |
| WO | WO2008044011 | 4/2008 |
| WO | WO2008089172 | 7/2008 |
| WO | WO2008098019 | 8/2008 |
| WO | WO2008101932 | 8/2008 |
| WO | WO2008112912 | 9/2008 |
| WO | WO2008131197 | 10/2008 |
| WO | WO2008134264 | 11/2008 |

OTHER PUBLICATIONS

Andriano, et al., 'Processing and characterization of absorbable polylactide polymers for use in surgical implants,' Journal of Applied Biomaterials, 5(2):133-140 (1994).

Asano, et al., 'In vivo characteristics of low molecular weight copoly(D,L-lactic acid) formulations with controlled release of LH-RH agonist,' Biomaterials, 10(8):569-573 (1989).

Barca, et al., 'Resorbable poly-L-lactic acid mini-staples for the fixation of Akin osteotomies,' The Journal of Foot and Ankle Surgery, 36(2):106-111 (1997).

Bertrand, et al., 'Biocompatbility Aspects of New Stent Technology,' JACC, 32(3):562-571 (1998).

Celikkaya, et al., 'Poly(DL-lactide)/Poly(ethylene glycol) Copolymer Particles. I. Preparation and Characterization,' Journal of Applied Polymer Science, 61:1439-1446 (1996).

Daniels, et al., 'Mechanical properties of biodegradable polymers and composites proposed for internal fixation of bone,' J. Applied Biomaterials, 1:57-78 (1990).

Dauner, et al. 'Resorbable continuous-fiber reinforced polymers for osteosynthesis,' J. Materials Science Materials in Medicine, 9:173-179 (1998).

Eling, et al., 'Biodegradable Materials of Poly(L-Lactic Acid): 1. Melt-Spun and Solution-Spun Fibres,' Polymer, 23:1587-1593 (1982).

Fambri, et al., 'Biodegradable fibres of poly(l-lactic acid) produced by melt spinning,' Polymer, 38:79-85 (1997).

Frenger, 'Biomedical Uses of Shape Memory Polymers,' Biomed. Sci. Instrum., 29:47-50 (1993).

Fukuzaki, et al., 'Synthesis of copoly(D,L-Lactic acid) with relatively low molecular weight and in vitro degradation, Japan Atomic Energy Research Institute, Gunma, Jpn, European Polymer Journal, 25(10):1019-1026 (1989).

Giardino, et al., 'Experimental evaluation of a resorbable intramedullary plug for cemented total hip replacement,' Biomaterials, 18(13):907-913 (1997).

Gautier, et al., 'Poly($\alpha$-hydroxyacids) for application in the spinal cord: Resorbability and biocompatibility with adult rate Schwann cells and spinal cord,' Journal of Biomedical Materials Research, 42(4):642-654 (1998).

Gogolewsji, et al., 'Resorbable materials of poly(L-lactide). II Fibers spun from solutions of poly(L-lactide) in good solvents,' J. Appl. Polymer Sci., 28:1045-1061 (1983).

Grijpma, et al., 'Chain Entanglement, Mechanical Properties and Drawability of Poly(Lactide),' Colloid. Polym. Sci., 272:1068-1081 (1994).

Gupta, et al., 'Poly(lactic acid) fiber: An overview' Progress in Polymer Science, Pergamon Press, Oxford, GA, 34(4):455-482 (2007).

Haers, et al., 'Biodegradable polyactide plates and screws in orthognathic surgery,' Journal of Cranio-Maxillofacial Surgery, 26(2):87-91 (1998).

L. L. Hench, et al., 'Bioactive materials: The potential for tissue regeneration,' J. Biomed. Materials Research, 41(4):511-518 (1998).

D. Hull and T. W. Clyne, 'An introduction to composite materials,' Second Edition, Cambridge University Press, Table of Contents, 8 pages.

Hyon, et al., 'Effects of residual monomer on the degradation of DL-lactide polymer,' Hyon, Jamshidi & Ikada, Polymer International, 46:196-202 (1998).

Kaitian, et al., 'Poly(D,L-Lactic Acid) Homopolymers: Synthesis and Characterization,' Turkish Journal of Chemistry, 20:43-53 (1996).

Kister, et al., 'Effects of morphology, conformation and configuration on the IR and Raman spectra of various poly(lactic acid)s,' Polymer, 39(2): 267-273 (1998).

Koelling, et al., 'In vitro real-time aging and characterization of poly(L/D-lactic acid),' Proceedings of the 1997 16th Southern Biomedical Engineering Conference (Cat. No. 97TH8270), pp. 197-201.

Kontio, et al., 'Fibrous wound repair associated with biodegradable poly-L/d-lactide copolymers implants: study of the expression of tenascin and cellular fibronectin,' Journal of Materials Science-Materials in Medicine, 9:10:603-609 (1998).

Kricheldorf, et al., 'Polyactones: 32. High-molecular weight polylactides by ring-opening polymerization with dibutylmagnesium or butylmagnesium chloride,' Polymer, 36(15):2995-3003 (1995).

Losken, et al., 'Memory of DL-polylactic acid biodegradable plates,' Ann. Plast. Surg., 32(6):606-611 (1994).

MacDonald, et al., 'Enzymatic degradability of poly(lactide): Effects of chain stereochemistry and material crystallinity,' Macromolecules, 29(23):7356-7361 (1996).

Mainil-Varlet, et al., 'Effect of in vivo and in vitro degradation on molecular and mechanical properties of various low-molecular weight polylactides,' Journal of Biomedical Materials Research, 36(3):360-380 (1997).

Matsumura, et al., 'Novel ring opening polymerization of lactide by lipase,' Macromol. Symp., 130:285-304 (1998).

Morita, et al., 'Intravitreous delivery of dexamethasone sodium m-sulfobenzoate from poly(DL-lactic acid) implants,' Biological & Pharmaceutical Bulletin, 21(2):188-190 (1998).

(56) References Cited

OTHER PUBLICATIONS

Okihara, et al., 'Crystal structure of stereocomplex of poly(L-lactide) and poly(D-lactide), Journal of Macromolecular Science-Physics, B30(1-2):119-140 (1991).

Okuzaki, et al., Mechanical Properties and Structure of the Zone-Drawn Poly(L-lactic acid) Fibers, Journal of Polymer Science, Part B, Polymer Physics, 37:991-996 (1999).

Oriented Polymer Materials, Edited by Stoyko Fakirov, published by Huthig & Wepf Verlag Zug, Heidelberg, Oxford CT/USA, Table of Contents pp. v, viii, ix-xix (1996).

Penning, et al., 'Preparation and properties of absorbable fibres from L-lactide copolymers,' Polymer, 34(5):942-951 (1993).

Pitt, et al., 'Modification of the rates of chain cleavage of poly($\epsilon$-caprolactone) and related polyesters in the solid state,' Journal of Controlled Release, 4:283-292 (1987).

Pitto, et al., "Comparison of fixation of the femoral component without cement and fixation with use of a bone-vacuum cementing technique for the prevention of fat embolism during total hip arthroplasty," J. Bone Joint Surg., 81-A(6):831-843 (1999).

Rak, et al., 'The preparation and characterization of poly(DL-lactic acid) for use as a biodegradable drug carrier,' Liverpool Polytech., Liverpool, UK, Pharmaceutica Acta Helvetiae, 60:(5-6):162-169 (1985).

Ristic, et al., 'An investigation of synthesis and degradation of poly(D,L-lactide) and controlled release of albumin from biodegradable poly(D,L-lactide) cylinders,' ICheaP-2, the second Italian conference on chemical and process engineering, Florence, pp. 559-563 (1995).

Schliephake, et al., 'Reconstruction of the mandible by prefabricated autogenous bone grafts,' Int. J. Oral Maxillofac. Surg., 26:244-252 (1997).

Stahelin, et al., 'Clinical degradation and biocompatibility of different bioabsorbable interference screws: a report of six cases,' Arthroscopy: The Journal of Arthroscopic & Related Surgery, 13(2):238-244 (1997).

Steendam, et al., 'The role of elastic relaxation in drug delivery from poly(DL-lactic acid) based tablets. A shape memory phenomenon,' Proceedings of the International Symposium on Controlled Release of Bioactive Materials, 25:128-129 (1998).

Stevels, et al., 'Blends van blok copolymeren die een poly(L-lactide) of poly(D-lactide) blok bevatten,' Biomedical Science and Engineering Meeting, pp. 107-110 (1994).

Tagil, "Thesis—The morselized and impacted bone graft animal experiments on proteins, impaction and load," Acta Orthop. Scand. Suppl., 290:1-40 (2000).

Temenoff and Mikos, "Injectable biodegradable materials for orthopedic tissue engineering," Biomaterials, 21:2405-2412 (2000).

Tschakaloff, et al., 'Degradation kinetics of biodegradable DL-polyactic acid biodegradable implants depending on the site of implantation,' International Journal of Oral and Maxillofacial Surgery, 23(6 Pt2):443-445 (1994).

Tsuji, et al., 'Stereocomplex formation between enantiomeric poly(lactic acid). VIII. Complex fibers spun from mixed solution of poly(D-lactic acid) and poly(L-lactic acid), Journal of Applied Polymer Science, 51(2):337-344 (1994).

J. West, J. Hubbell, 'Bioactive Polymers, Synthetic biodegradable polymer scaffolds,' Chapter 5, pp. 83-95, Anthony Atala and David J. Mooney, Editors; Joseph P. Vacanti and Robert Langer, Associate Editors, Birkhauser (1997).

D. Wheeler, et al., 'Effect of bioactive glass particle size on osseous regeneration of cancellous defects,' J. Biomed. Materials Research, 41(4):527-533 (1998).

Zegzula, et al., 'Bone Formation with Use of rhBMP-2 (Recombinant Human Bone Morphogenetic Protein-2,' The Journal of Bone and Joint Surgery, 79:1778-1790 (1997).

Zhang, 'Biodegradable lactide polymers: synthesis, degradation, and controlled drug release properties (drug release), Queen's University at Kingston, Canada, vol. 55/01-B of Dissertation Abstracts International, p. i-xv, 1-179 (Oct. 1993).

Structure and Properties of Orientated Polymers, Ed. I. M. Ward, Department of Physics, University of Leads, England, a Halsted Press Book, John Wiley & Sons, New York-Toronto (1975) Table of Contents.

International Search Report; International PCT Application No. PCT/US2007/086067; Aug. 13, 2008; 5 pages.

International Preliminary Report on Patentability and Written Opinion; International PCT Application No. PCT/US2007/086067; Jun. 3, 2009; 11 pages.

Patent Examination Report No. 1, Australian Patent Application No. 2007325001, Jun. 26, 2012; 4 pages.

* cited by examiner

FIBER REINFORCED COMPOSITE MATERIAL

CROSS-REFERENCE TO RELATED APPLICATIONS

This application is the U.S. national phase of International Application No. PCT/US2007/086067 filed on Nov. 30, 2007 published in English on Jun. 5, 2008 as International Publication No. WO 2008/067531 A1, which application claims the benefit of U.S. Provisional Application Ser. No. 60/867,978 filed Nov. 30, 2006, the entire contents of both of which are hereby incorporated by reference.

BACKGROUND OF THE INVENTION

1. Field of the Invention

The present disclosure relates to bioresorbable composites and more specifically to a fiber reinforced polymer composite material that is used to make bioresorbable products.

2. Related Art

Metal products have been used in fracture fixation due to their high strength. While these products perform well, there are a significant number of occurrences where these products can cause problems to the patient. In some cases the presence of the metal implant can cause irritation of the soft tissue around the implant, in severe cases this necessitates the removal of the implant. The procedure to remove the metal products exposes the patient to the risks associated with undergoing a major medical procedure and also adds to the overall cost of healing the original fracture. One potential solution to substantially reduce the need to remove fracture fixation hardware is to use bioresorbable devices to fix the fracture. However, the currently available bioresorbable materials and products do not have the required combination of initial strength and retention of this strength for suitable fracture healing to occur.

The currently marketed bioresorbable products include those products manufactured from injection molded polymers, polymer blends, and co-polymers. These products have been utilized in the areas of craniomaxilofacial implants and non-load bearing fracture fixation implants, such as pins and screws, for wrist and ankle applications and for reattaching soft tissues, such as ligaments and tendons, to bone. In addition, there are also some spinal products available that make use of the compressive properties of these polymers. Products including these materials are easy to process, but are limited by the mechanical properties of the materials. These materials have a tensile strength in the range of between about 50 MPa to about 100 MPa. Depending on the choice of polymer or co-polymer, products in this category retain the majority of their strength for less than about 12 weeks. Therefore, these materials are not suitable for fracture fixation applications beyond simple non-loaded pins and screws.

Other currently marketed bioresorbable products include self reinforced products that have improved strength due to orientation of the polymer during processing of the product. Even though these products have improved strength, their flexural strength is still only around 250 MPa. This limits the uses of this technology for fracture fixation to screws and pins.

Recently, devices have been manufactured from fiber reinforced polymer composites utilizing polyglycolic acid (PGA) fibers. These composites have a good initial strength, but suffer a rapid loss in strength due to the rapid hydrolysis of these fibers. Devices have been manufactured using PLLA fibers and PDLLA as the matrix material. Unfortunately, this matrix breaks down rapidly and results in the composites having a rapid loss in strength. Other attempts have used co-polymers containing PLLA as the reinforcing fiber, such as PLLA-co-PGA copolymers at a ratio of 82:18. However, there has been difficulty in finding a suitable polymer matrix material that can be processed into a composite without degrading or breaking this reinforcing fiber. Most recently, composites have been made where the matrix was a polymer with the same chemical composition as the fiber or where the matrix was a blend with the majority of the blend being a polymer with the same chemical composition as the matrix. These composites have an initial flexural strength of between 120 to 140 MPa, with most of this strength lost within about 12 weeks of use.

Attempts to slow down the degradation of the polymer matrix have included modifying the composition to increase the hydrophobicity of the polymer. However, this increases either the crystallinity of the polymer matrix, which is undesirable from a biological perspective, or it makes the polymer too ductile if a hydrophobic rubbery component, such as polycaprolactone (PCL), is added. Buffering materials, such as calcium carbonate, have also been added to polymers to slow degradation rates and improve the biological properties, such as osteoconductivity. However, in order to gain the beneficial effects of calcium carbonate it needs to be present at high levels, about 30% by weight of the composition. Since a fiber polymer composite contains at least 50% of fiber by volume, it would be anticipated that a calcium carbonate-containing matrix would interfere adversely with the interface between the polymer matrix and reinforcing fibers. This could result in the fiber-reinforced composite substantially weakening or even falling apart before complete healing of a fracture.

In order to make a suitable fiber-reinforced composite material, the fiber and matrix material have certain requirements. The fiber needs to have both a high initial tensile strength, and the ability to retain the majority of this strength, for the fracture to heal. To have a high initial strength, the fibers need to be highly orientated and be present at about 40% by volume of the composite. In addition, the fibers should also have some crystallinity, as this imparts stability against relaxation of the orientation in the fiber.

The matrix material also needs to be able to retain the majority of its strength for a suitable time, approximately between about 6 to about 12 weeks, for the fracture to heal. In order to accomplish this, the matrix should have a sufficiently high initial molecular weight. As the polymers degrade, the molecular weight decreases and the polymers become brittle and lose their mechanical properties. Additives, such as calcium carbonate or other buffering materials, can be added to the matrix to control the degradation rate. The amount of the buffering material should be around 30% by weight of the matrix without adversely interfering with the interface between the polymer matrix and the reinforcing fibers.

In addition, the matrix material needs to be processable at a temperature which is low enough to not significantly affect the strength of the fiber and adhere well enough to the fiber to allow stress transfer from the matrix to the fiber. To accomplish this, both semi-crystalline and amorphous co-polymers can be used. Semi-crystalline co-polymers are typically composed of lactic acid and one or more additional monomer units whose function is to lower the melting point of the co-polymer matrix to a point where the strength of the fiber is not affected during the consolidation step. Amorphous or non-crystalline materials, such as poly (D-lactide) acid polymers, are suitable for processing with the fiber, as they soften at relatively low temperatures. However, these materials do not have a long strength retention time. This strength retention can be improved by incorporating a buffering material, such as calcium carbonate, into the matrix material. In this case, the calcium carbonate acts as both a buffer and also reduces the thermal sensitivity of the polymer to breakdown during processing. Taken together, the affect of the calcium carbonate is to both slow the rate of degradation of the polymer and help preserve the molecular weight during processing, without adversely interfering with the interface between the polymer matrix and the reinforcing fibers.

The present disclosure incorporates these requirements to produce a bioresorbable material which has a high initial strength and retains a significant proportion of this strength for a useful time.

SUMMARY OF THE INVENTION

In one aspect, the present disclosure relates to a fiber reinforced composite material including a PLLA fiber material, such as a continuous PLLA fiber material, and a matrix material that does not have the same chemical element composition as the fiber material. In an embodiment, the composite further includes a degradation controlling agent dispersed in the matrix material. In another embodiment, the degradation controlling agent includes a buffer material selected from a group including calcium carbonate, calcium hydrogen carbonates, calcium phosphates, tricalcium phosphates, dicalcium phosphates, magnesium carbonate, and sodium carbonate. In yet another embodiment, the degradation controlling agent includes a common salt. In an embodiment, the degradation controlling agent is selected from a group including a buffer material, a common salt, and combinations thereof. In a further embodiment, the degradation controlling agent is between about 0.1% to about 40% by weight of the matrix material. In yet a further embodiment, the composite further includes an accelerant dispersed in the fiber or matrix material. In a further embodiment, the PLLA fiber material is about 50% by volume of the composite. In an embodiment, the fiber material, which is bioabsorbable, has a tensile strength of between about 500 MPa to about 2000 MPa and a molecular weight of between about 290,000 g/mol and about 516,000 g/mol.

In an embodiment, the matrix material is bioresorbable and is selected from a group including a polymer, a copolymer, and a polymer blend. In another embodiment, when a polymer blend is used as the matrix, the blend includes at least two polymers and at least one of the polymers has a chemical element composition that is different to that of the fiber. In yet another embodiment, the polymer having a chemical element composition that is different to that of the fiber comprises at least 50% of the polymer blend. In a further embodiment, the polymer having a chemical element composition that is different to that of the fiber comprises more than 50% of the polymer blend. In yet a further embodiment, the matrix material is bioabsorbable.

In yet a further embodiment, the composite has an initial tensile strength of at least 250 MPa and retains at least 75% of the initial tensile strength for at least 8 weeks. In an embodiment, the composite material includes a flexural strength of about 200 MPa and a shear strength of at least 140 MPa.

In another aspect, the present disclosure includes a fiber reinforced composite material having a matrix material, a glass fiber material, and a degradation controlling agent. In an embodiment, the matrix material is selected from a group including a polymer, a copolymer, and a polymer blend. In an embodiment, the matrix material is bioabsorbable. In another embodiment, the glass fiber material is bioabsorbable. In yet another embodiment, the glass fiber material includes a tensile strength between about 300 MPa and about 1200 MPa. In a further embodiment, the glass fiber material includes a hydrophobic material. In yet a further embodiment, the glass fiber material is about 50% by volume of the composite.

In an embodiment, the degradation controlling agent is dispersed in the matrix material. In another embodiment, the degradation controlling agent is coated on a surface of the fiber material. In yet another embodiment, the degradation controlling agent is between about 0.1% to about 40% by weight of the matrix material. In a further embodiment, the degradation controlling agent includes a buffer material selected from a group including calcium carbonate, calcium hydrogen carbonates, calcium phosphates, tricalcium phosphates, dicalcium phosphates, magnesium carbonate, and sodium carbonate. In yet a further embodiment, the degradation controlling agent includes a common salt. In an embodiment, the degradation controlling agent is selected from a group including a buffer material, a common salt, and combinations thereof.

In yet a further embodiment, the composite has an initial tensile strength of at least 250 MPa and retains the initial tensile strength for at least 8 weeks. In an embodiment, the composite includes an initial flexural strength of between about 250 MPa and about 400 MPa. In another embodiment, the composite includes an initial flexural modulus of between about 20-30 GPa. In yet another embodiment, the composite retains about 98% of an initial mass for at least 2 weeks.

In yet another aspect, the present disclosure includes a fiber reinforced composite material having a matrix material, a fiber material, and a degradation controlling agent.

In a further aspect, the present disclosure includes a fiber reinforced composite material having a matrix material and a glass fiber material, wherein the glass fiber material includes a tensile strength of between about 300 MPa and about 1200 MPa.

In yet a further aspect, the present disclosure includes a fiber reinforced composite material having a PLLA fiber material and a matrix material, wherein the fiber material includes a molecular weight of between about 290,000 g/mol and about 516,000 g/mol.

Further areas of applicability of the present disclosure will become apparent from the detailed description provided hereinafter. It should be understood that the detailed description and specific examples, while indicating the preferred embodiments of the disclosure, are intended for purposes of illustration only and are not intended to limit the scope of the disclosure.

DETAILED DESCRIPTION OF THE EMBODIMENTS

The following description of the preferred embodiment(s) is merely exemplary in nature and is in no way intended to limit the disclosure, its application, or uses.

In one aspect, the present disclosure relates to a fiber-reinforced composite material having a PLLA fiber material and a matrix material that does not have the same chemical element composition as the fiber material.

A continuous PLLA fiber is extruded and drawn to provide the fiber with a tensile strength of between about 500 MPa to about 2000 MPa and a molecular weight of between about 290,000 g/mol to about 516,000 g/mol. The extrusion and drawing process used to make the fiber may be any extrusion and drawing process known to one of ordinary skill in the art. The PLLA fiber material is about 50% by volume of the composite and is bioabsorbable.

The matrix material, which is bioabsorbable and selected from a group that includes a polymer, a copolymer, and a polymer blend, is then made. For the purposes of this disclosure, a matrix material that does not have the same chemical element composition as the fiber material is defined as the following: If the matrix material is a polymer, then the polymer may not be a pure polylactide material. If the matrix material is a copolymer, then at least one of the monomeric species is not a lactone monomer. If the matrix material is a polymer blend, then at least one of the polymers has a chemical element composition that is different to that of the fiber. The polymer that has a chemical element composition different to that of the fiber comprises at least 50% or more of the polymer blend. Alternatively, a matrix material that has the same chemical element composition as the fiber material, which is also within the scope of this disclosure, is defined as the following: If the matrix material is a polymer, then the polymer is a pure polylactide material. If the matrix material is a copolymer, then both monomeric species are lactone monomers. If the matrix material is a polymer blend, then both polymers are pure polylactide materials.

The composite may further include a degradation controlling agent. For the purposes of this disclosure, the degradation controlling agent may include a buffer material, a common salt, and combinations thereof. The buffer material is selected from a group including, but not limited to, calcium carbonate, calcium hydrogen carbonates, calcium phosphates, tricalcium phosphates, dicalcium phosphates, magnesium carbonate, and sodium carbonate. The common salt is water soluble and may be organic or inorganic. In addition, the salt may be based on, without limitation, one of the following: a Group I metal, including but not limited to, lithium, sodium, and potassium; a Group II metal, including but not limited to, beryllium, magnesium, calcium, strontium, and barium; transition metals, including but not limited to, copper, zinc, silver, gold, iron, and titanium; a Group III metal, including but not limited to, aluminum and boron. Furthermore, the salt may include, without limitation, a carbonate, a hydrogen carbonate, a phosphate, a hydrogen phosphate, silicates, polyphosphates, and polysilicates. Finally, the salt may be a single element, a compound, or a mixture thereof.

The degradation controlling agent is dispersed in the matrix material and is used as a buffer agent and to slow the degradation of the composite. The degradation controlling agent is between about 0.1% to about 40% by weight of the matrix material. The composite may further include an accelerant, such as the tertiary butyl ester of lauric acid or the ditertiary butyl ester of fumaric acid, dispersed in the matrix material or fiber material. Other accelerants known to those of ordinary skill in the art may be used. Use of these accelerants accelerates the degradation rate of the fiber or matrix.

The composite material has an initial tensile strength of at least 250 MPa and retains at least 75% of this initial tensile strength for at least 8 weeks. For the purposes of this disclosure, an initial tensile strength is taken to mean the tensile strength of the composite material prior to degradation. In addition, the composite has a flexural strength of about 200 MPa and a shear strength of at least 140 MPa.

In another aspect, the present disclosure relates to a fiber-reinforced composite material including a matrix material, a glass fiber material, and a degradation controlling agent.

The matrix material may be any biodegradable polymer, polymer blend, copolymer, or other biodegradable material known to those skilled in the art. Examples of biodegradable polymers include alpha-polyhydroxy acids, polyglycolide (PGA), poly(L-lactide), poly(D,L-lactide), poly(.epsilon.-caprolactone), poly(trimethylene carbonate), poly(ethylene oxide) (PEO), poly(.beta.hydroxybutyrate) (PHB), poly(.beta.-hydroxyvalerate) (PHVA), poly(p-dioxanone) (PDS), poly(ortho esters), tyrosine-derived polycarbonates, polypeptides, polyurethane, and combinations thereof.

The glass fiber material is bioabsorbable and represents about 50% by volume of the composite. The glass fiber material may be extruded and drawn by any extrusion and drawing process known to one of ordinary skill in the art. The fiber includes a tensile strength of between about 300 MPa and about 1200 MPa. In addition, the fiber material may include a hydrophobic material to slow down the degradation of the glass fiber material. The hydrophobic material may be a component of the composition of the glass fiber material or coated on a surface of the glass fiber material. Examples of hydrophobic materials include, without limitation, polycaprolactone, poly-para-xylylene (e.g. Parylene), isomers and co-polymers of polylactide, polypeptide, ceramic materials (i.e. hydroxyapatite and any form of calcium phosphate), and any other organic or inorganic hydrophobic material likely to slow down the penetration of water to the fiber. For the purposes of this disclosure, the glass fibers include about 50 mol % potassium oxide ($P_2O_5$), about 30 mol % calcium oxide (CaO), about 15 mol % sodium oxide ($Na_2O$), and 5 mol % iron oxide ($Fe_2O_3$). However, glass fibers of different compositions may be used.

The degradation controlling agent may be of the same type as the degradation controlling agents described above and may be dispersed in the matrix material or coated on a surface of the fiber material. The agent acts as a means to control the degradation of the composite and/or the glass fiber. Specifically, with regards to the glass fibers, it is believed that the common salt substantially reduces the release of ions from the fibers. Where the degradation controlling agent is dispersed in the matrix material, the agent represents between about 0.1% to about 40% by weight of the matrix material.

The composite has an initial tensile strength of at least 250 MPa and is able to retain this initial tensile strength for at least 8 weeks. In addition, the composite includes an initial flexural strength of between about 250 MPa and about 400 MPa. Furthermore, the composite retains about 98% of an initial mass for at least 2 weeks when it is placed in in-vivo conditions.

The reinforcing fibers of both composites, as described above, preferably have mechanical properties that are not substantially compromised when tested in a physiological (aqueous, 37° C.) environment. The fibers are preferably insoluble in the solvent used to dissolve the matrix polymer. In addition, the degradation controlling agent of both composites must be one that reacts with the acid by-products that are generated during the degradation of the polymer fiber or matrix or the glass fiber, including, without limitation, lactic acid, glycolic acid, caproic acid, and different forms of phosphoric acid. Where the degradation controlling agent is in a particulate form, the particles may have a number of sizes, ranging from about 1 mm to about 10 nm, and geometries, such as needle, cubic, platelet, fibers, spheres, and other geometries known to one of ordinary skill in the art. It is important, but not required, that the particles have a shape that enhances the mechanical properties of the particles.

Biological agents, such as cells, growth factors, antibiotics, anti-microbials, or other such factors may be added to one or more components of the composites to promote healing of the fracture.

Further details may be derived from the examples below.

EXAMPLE 1

PLLA fiber was first made by taking PLLA granules with a nominal intrinsic viscosity of 3.8 and extruding the granules into a fiber. A single screw extruder fitted with a gear pump and a 2 mm spinneret die was used. The extruder also had a provision for air cooling. The extruded fiber was batched on spools for the next processing step. Subsequently, the fiber was progressively stretched at elevated temperatures to produce a final diameter of ca. 100 microns and a draw ratio between about 8 and about 15. The final molecular weight of the drawn fiber was between about 290,000 g/mol$^{-1}$ to about 516,000 gmol$^{-1}$. The resultant fiber had an average tensile strength of greater than about 800 MPa.

Composites were then made using an 85:15 co-polymer of PDLLA and PGA with a 35% weight addition of calcium carbonate (CaCO$_3$) as the matrix material. The drawn poly (L-lactide) fibers were then wound around a support frame of parallel bars that were held a constant distance apart. For each sample the fiber was wrapped 75 times around the support frame, resulting in 150 fibers in each composite. The matrix was dissolved in a solvent, methyl acetate, at 10% wt/vol of solvent. The solvent/polymer mixture was then coated onto the fibers. The composite was then placed in a vacuum oven at 40° C. for 12 hours to remove the solvent.

The composite was then placed in a cylindrical mold and heated to 165° C. This temperature is used to melt the matrix material to allow it to flow and consolidate the composite. Once thermal equilibrium was reached, slight tension was applied to the fibers to align them in the mold. The mold was then closed completely to consolidate the fibers and the matrix. The closed mold was then maintained at 165° C. for up to 5 minutes and then removed from the heated press and placed between cool metal blocks to cool the composite down to room temperature to allow tension to be released from the fibers.

Samples of the composite were aged in phosphate buffer solution (PBS) at 37° C. The average diameter of the samples was about 1.7 mm. The composites were removed from the aging solution, dried, and tested using a 3-point bend test method. As shown in Table 1, the samples were tested for their initial tensile strength and their tensile strengths after 6, 10, 12, and 16 weeks. Compared to the initial tensile strength, the tensile strength of the composite during the succeeding weeks remained high.

TABLE 1

| Week | Tensile strength/MPa |
|---|---|
| 0 | 325 |
| 6 | 319 |
| 10 | 338 |
| 12 | 291 |
| 16 | 315 |

EXAMPLE 2

Composites were made using the method described in Example 1, with and without CaCO$_3$ mixed in the matrix, and with a range of different matrix materials. The resultant composites were tested for their flexural strength in 3 point bending. The pins were 2 mm in diameter and tested using a 16:1 span to diameter ratio. The results are given in Table 2. It is clear that the mechanical properties of the composites containing a degradation controlling agent are not significantly compromised by the presence of the material.

TABLE 2

| Matrix material | Composite flexural strength/MPa |
|---|---|
| PLLA-co-PGA (85:15) | 342 |
| PLLA-co-PGA (82:18) | 299 |
| PLLA-co-PGA (82:18) + 30 wt % CaCO$_3$ | 311 |
| PDLA-co-PGA (85:15) + 35 wt % CaCO$_3$ | 323 |

EXAMPLE 3

Composites were made that included poly-L-lactic acid (PLLA) fibers and a co-polymer matrix of poly-L-lactic acid (PLLA) and polyglycolic acid (PGA) (PLGA 85:15) using the method described in example 1. The composite did not include calcium carbonate or other degradation controlling agents. The flexural and shear properties of the resultant pins were tested, via a 3-point bending test, after aging in PBS at 37° C. The results are given in Table 3.

TABLE 3

| Week | Flexural Strength/MPa | Shear Strength/MPa |
|---|---|---|
| 0 | 251 | 192 |
| 6 | 261 | 187 |
| 12 | 172 | 190 |
| 18 | 185 | 173 |
| 24 | 87 | 158 |

EXAMPLE 4

40 g of poly(D,L-lactide-co-glycolide) were dissolved in 360 ml of CHCl$_3$ to produce a clear solution and 61.54 g of calcium carbonate (CaCO$_3$) filled poly(D,L-lactide-co-glycolide) were dissolved in 360 ml of CHCl$_3$ to produce a suspension of CaCO$_3$ particles in polymer solution. 1 m long skeins of glass fiber, having the properties shown in Table 4 and weighing between 4.56 g and 7.32 g, were then dipped in the solutions and suspended in a fume cupboard to allow the solvent to evaporate. The resulting coated fiber strips were vacuum dried at 80° C. below 1 mbar to constant mass. The weights and compositions of the dried skeins are shown in Table 5.

TABLE 4

| Fibre | A | B | C |
|---|---|---|---|
| Number of specimen | n = 15 | n = 16 | n = 11 |
| Diameter (μm) | 18 ± 5 | 36 ± 6 | 24 ± 5 |
| Tensile strength at break (MPa) | 1200 ± 320 | 560 ± 190 | 313 ± 280 |
| Tensile Chord Modulus (GPa) (0.1% to 0.3% strain) | 101 ± 18 | 82 ± 24 | 39 ± 15 |

TABLE 5

| Coating solution | Skein (g) | Coated skein (g) | Fibre (% v/v) |
|---|---|---|---|
| Filled Poly(D,L-lactide-co-glycolide) | 5.75 | 9.45 | 53.7 |
|  | 7.32 | 9.95 | 67.5 |
| Poly(D,L-lactide-co-glycolide) | 4.56 | 6.31 | 58.0 |
|  | 6.68 | 8.58 | 65.1 |

The coated fiber strips were cut into 120 mm lengths and compression molded at 160° C. to produce composite bars with nominal measurements of 10×3×120 mm. The bars were accurately measured and weighed to calculate their compositions. The flexural mechanical properties of the composites were tested using a 3 point bend test method. The length/distance ratio of the composites was 32 and the test speed was 4.74 mm/min. The moduli were determined from 3 measurements and the strength/strain to failure from 1 specimen. The compositions and mechanical properties results are shown in Table 6. The table shows that the glass fiber composites have substantially similar flexural strengths to the polymer fiber composites in Table 2. For the purposes of this disclosure, the modulus is a quantity that expresses the degree to which a substance possesses a property, such as elasticity.

TABLE 6

| Matrix polymer | Fibre (% v/v) | Modulus (Gpa) | Strength (Mpa) | Strain to failure (%) |
|---|---|---|---|---|
| Filled Poly(D,L-lactide-co-glycolide) | 60.6 | 26.6 ± 1.1 | 297.4 | 1.1 |
| Poly(D,L-lactide-co-glycolide) | 61.6 | 25.9 ± 0.3 | 297.1 | 1.2 |

EXAMPLE 5

Solutions of 10% w/w of poly (D-L-lactide-co-glycolide) 85:15 and 35% w/w (of the polymer weight) CaCO3 in $CH_2Cl_2$ were prepared. Approx. 50 cm lengths of glass fiber (50 mol % $P_2O_5$, 30-40 mol % CaO, 5-15 mol % $Na_2O$, 5 mol % $Fe_2O_3$) weighing between 1.5 and 7 g were weighed, dipped in the polymer solution, and hung up to dry in a fume cupboard over night. The fibers were then vacuum dried at 80° C. and re-weighed. The composite strips were cut into 12 mm lengths and randomized.

The composites were compression moulded in an aluminium mould with a cavity measuring 120×3×10 mm. The mould was lined with a strip of PTFE impregnated glass cloth to allow the product to be removed more easily. The moulding was done at 160° C. under 100 kN pressure. The mould was pre-heated and then strips were loaded into the cavity by hand one or two at a time. Once the mould was full, the pressure was applied for a few seconds, the mould was then re-opened, and further strips added. This was repeated until no further strips could be forced into the mould. The mould was then cooled to room temperature under pressure. The composite bars were trimmed and then capped with a layer of filled matrix to seal the ends. The weights and compositions of the fibers are shown in Table 7.

All samples were tested to assess flexural stiffness and tested to failure. Tests were performed in a 3 point bending test set-up, with a testing span of 90 mm and thickness and width measured for each sample. For modulus measurements, deflection was performed at a crosshead displacement of 4.74 mm/min using a 100N load cell. Strength was measured using a 10 kN load cell. The compositions and mechanical properties results are shown in Table 8.

TABLE 8

| Composite type | Flexural strength (MPa) | Flexural modulus (GPa) |
|---|---|---|
| 15% Na2O | 272.2 ± 31.0 | 26.8 ± 1.7 |
| 5% Na2O | 334.6 ± 22.5 | 27.3 ± 1.9 |

EXAMPLE 6

Glass fiber composites, as prepared in Example 5, with and without CaCO3 filler mixed in the matrix, were immersed individually in bottles containing 300 ml of phosphate buffer saline (PBS) and placed in an incubator at 37° C. The samples were removed for analysis after 14 days, and their dry mass was recorded. The samples containing CaCO3 had retained 98% of their initial dry mass, while those without CaCO3 had only retained 63% of their initial dry mass The polymer fiber composite material of the present disclosure includes a polylactic acid fiber of high strength and a matrix material that is suitable for working with this fiber. The matrix allows for a good interfacial strength between the fiber and the matrix, which provides the composite with a high mechanical strength and a decreased degradation rate. Also disclosed are polymer and glass fiber composite materials having a concentration of buffering material that has been shown to not adversely interfere with the interface between the polymer matrices and the fiber materials. Rather, the testing results show that the buffering material works to provide the composite with the ability to retain a majority of its initial strength over a longer period of time by slowing the rate of degradation of the polymer matrix and, in the glass fiber composite, the degradation rate of the glass fiber.

A composite material containing a matrix material and a mixture of the above-described glass and polymer fibers, with or without a degradation controlling agent, is also within the scope of this disclosure. The matrix and the glass and polymer fibers may be of the same type and made by the same processes as the above-described matrices and polymer/glass fibers. In addition, the degradation controlling agents may be of the same type as described above. Furthermore, the processing conditions for making the composite may be the same as the processing conditions for making the above-described polymer fiber composites.

As various modifications could be made to the exemplary embodiments, as described above with reference to the corresponding illustrations, without departing from the scope of

TABLE 7

| Composite type | n | Weight (g) Before end-capping | | Volume (mL) | | Density (g/mL) | | Fiber fraction (% v/v) | | | |
|---|---|---|---|---|---|---|---|---|---|---|---|
| | | Mean | Standard Deviation (SD) | Mean | Standard Deviation (SD) | mean | Standard Deviation (SD) | Mean | Standard Deviation (SD) | Max | Min |
| 15% Na2O | 11 | 7.1146 | 0.2102 | 3.34 | 0.06 | 2.13 | 0.06 | 69.9 | 5.8 | 76.2 | 57.4 |
| 5% Na2O | 13 | 6.9774 | 0.1987 | 3.30 | 0.09 | 2.12 | 0.03 | 67.9 | 3.5 | 74.3 | 63.6 | the disclosure, it is intended that all matter contained in the foregoing description and shown in the accompanying drawings shall be interpreted as illustrative rather than limiting. Thus, the breadth and scope of the present disclosure should not be limited by any of the above-described exemplary

What is claimed is:

1. A fiber reinforced composite material comprising:
   a matrix material selected from the group consisting of a polymer, a copolymer and a polymer blend;
   a fiber material; and
   a degradation controlling agent, wherein the degradation controlling agent is selected from the group consisting of buffer materials, common salts, and combinations thereof; and
   wherein the composite material has an initial tensile strength of at least 250 MPa.

2. The composite material of claim 1, further comprising a degradation accelerant dispersed in the matrix material.

3. The composite material of claim 1, wherein the buffer material is selected from the group consisting of calcium carbonate, calcium hydrogen carbonates, calcium phosphates, dicalcium phosphates, tricalcium phosphates, magnesium carbonate, and sodium carbonate.

4. The composite material of claim 1, further comprising a degradation accelerant dispersed in the fiber material.

5. The composite material of claim 1, wherein the degradation controlling agent consists of common salts.

6. The composite material of claim 1, wherein the degradation controlling agent consists of combinations of buffer materials and common salts.

7. The composite material of claim 1, wherein the degradation controlling agent consists of a buffer material.

8. The composite material of claim 7, wherein the buffer material consists of calcium carbonate.

9. The composite material of claim 7, wherein the buffer material consists of calcium hydrogen carbonates.

10. The composite material of claim 7, wherein the buffer material is selected from the group consisting of calcium phosphates, dicalcium phosphates and tricalcium phosphates.

11. The composite material of claim 7, wherein the buffer material consists of magnesium carbonate.

12. The composite material of claim 7, wherein the buffer material consists of sodium carbonate.

13. A fiber reinforced composite material comprising:
    a PLLA fiber material;
    a matrix material that does not have the same chemical element composition as the fiber material; and
    a degradation controlling agent dispersed in the matrix material; and
    a degradation accelerant dispersed in the PLLA fiber material.

14. The composite material of claim 13, wherein the degradation controlling agent comprises a buffer material selected from the group consisting of calcium carbonate, calcium hydrogen carbonates, calcium phosphates, dicalcium phosphates, tricalcium phosphates, magnesium carbonate, and sodium carbonate.

15. The composite material of claim 13, wherein the degradation controlling agent is a common salt.

16. The composite material of claim 13, wherein the matrix material comprises the degradation controlling agent in an amount of between about 0.1% and about 40% by weight.

17. The composite material of claim 13, wherein the degradation controlling agent is selected from the group consisting of buffer materials, common salts, and combinations thereof.

18. The composite material of claim 13, wherein the PLLA fiber material comprises a continuous PLLA fiber material.

19. The composite material of claim 13, wherein the PLLA fiber material is bioabsorbable.

20. The composite material of claim 13, wherein the matrix material is selected from the group consisting of polymers, copolymers, and polymer blends.

21. The composite material of claim 13, wherein the matrix material is bioabsorbable.

22. A fiber reinforced composite material comprising:
    a PLLA fiber material;
    a matrix material that does not have the same chemical element composition as the fiber material; and
    a degradation accelerant dispersed in the matrix material; and
    a degradation accelerant dispersed in the PLLA fiber material.

23. The composite material of claim 22, wherein the PLLA fiber material comprises a continuous PLLA fiber material.

24. The composite material of claim 22, wherein the fiber material is bioabsorbable.

25. The composite material of claim 22, wherein the matrix material is selected from the group consisting of polymers, copolymers, and polymer blends.

26. The composite material of claim 22, wherein the matrix material is bioabsorbable.

27. A fiber reinforced composite material comprising:
    a PLLA fiber material;
    a matrix material that does not have the same chemical element composition as the fiber material; and
    a degradation accelerant dispersed in the matrix material or a degradation controlling agent dispersed in the matrix material; and
    wherein the matrix material is selected from the group consisting of polymers, copolymers, and polymer blends; and
    wherein the polymer blend comprises at least two polymers, wherein at least one of the at least two polymers has a chemical element composition that is different to that of the fiber.

28. The composite material of claim 27, wherein the polymer blend comprises the polymer having a chemical element composition that is different to that of the fiber in an amount of at least 50% of the polymer blend.

29. The composite material of claim 28, wherein the polymer blend comprises the polymer having a chemical element composition that is different to that of the fiber in an amount of more than 50% of the polymer blend.

30. A fiber reinforced composite material comprising:
    a PLLA fiber material;
    a matrix material that does not have the same chemical element composition as the fiber material; and
    a degradation accelerant dispersed in the matrix material or a degradation controlling agent dispersed in the matrix material; and
    wherein the fiber material has a tensile strength of between about 500 MPa and about 2000 MPa.

31. The composite material of claim 30, wherein the fiber material has a tensile strength of about 800 MPa.

32. A fiber reinforced composite material comprising:
    a PLLA fiber material;
    a matrix material that does not have the same chemical element composition as the fiber material; and
    a degradation accelerant dispersed in the matrix material or a degradation controlling agent dispersed in the matrix material; and
    wherein the composite has an initial tensile strength of at least 250 MPa.

33. The composite material of claim 32, wherein the composite retains at least 75% of the initial tensile strength for at least 8 weeks.

34. A fiber reinforced composite material comprising:
a PLLA fiber material;
a matrix material that does not have the same chemical element composition as the fiber material; and
a degradation controlling agent dispersed in the matrix material; and
wherein the fiber material has a molecular weight of between about 290,000 g/mol and about 516,000 g/mol.

35. A fiber reinforced composite material comprising:
a PLLA fiber material;
a matrix material that does not have the same chemical element composition as the fiber material; and
a degradation accelerant dispersed in the matrix material or a degradation controlling agent dispersed in the matrix material; and
wherein the composite material comprises the PLLA fiber material in an amount of about 50% by volume.

36. A fiber reinforced composite material comprising:
a PLLA fiber material;
a matrix material that does not have the same chemical element composition as the fiber material; and
a degradation accelerant dispersed in the matrix material or a degradation controlling agent dispersed in the matrix material; and
wherein the fiber material has a molecular weight of between about 290,000 g/mol and about 516,000 g/mol.

37. A fiber reinforced composite material comprising:
a PLLA fiber material;
a matrix material that does not have the same chemical element composition as the fiber material; and
a degradation accelerant dispersed in the matrix material or a degradation controlling agent dispersed in the matrix material; and
wherein the composite has a flexural strength of about 200 MPa.

38. A fiber reinforced composite material comprising:
a PLLA fiber material;
a matrix materHial that does not have the same chemical element composition as the fiber material; and
a degradation accelerant dispersed in the matrix material or a degradation controlling agent dispersed in the matrix material; and
wherein the composite has a shear strength of at least 140 MPa.

* * * * *